United States Patent [19]
Frechette et al.

[11] Patent Number: 5,830,155
[45] Date of Patent: Nov. 3, 1998

[54] GUIDEWIRE ASSEMBLY

[75] Inventors: Robert Frechette, Fort Lauderdale; William R. Dorcas, Jr., Miami, both of Fla.

[73] Assignee: Cordis Corporation, Miami Lakes, Fla.

[21] Appl. No.: 549,157

[22] Filed: Oct. 27, 1995

[51] Int. Cl.⁶ .................................................. A61B 5/00
[52] U.S. Cl. ............................ 600/585; 604/45; 604/280
[58] Field of Search ................................. 128/772, 657, 128/658; 604/95, 96, 280, 281, 282

[56] References Cited

U.S. PATENT DOCUMENTS

| | | | |
|---|---|---|---|
| Re. 33,911 | 5/1992 | Samson et al. | 128/722 |
| 3,528,406 | 9/1970 | Jeckel et al. . | |
| 3,547,103 | 12/1970 | Cook . | |
| 3,706,883 | 12/1972 | McIntyre . | |
| 3,789,841 | 2/1974 | Antoshkiw . | |
| 3,847,157 | 11/1974 | Caillouette et al. . | |
| 4,279,252 | 7/1981 | Martin . | |
| 4,538,622 | 9/1985 | Samson et al. | 128/772 |
| 4,545,390 | 10/1985 | Leary . | |
| 4,554,929 | 11/1985 | Samson et al. . | |
| 4,616,653 | 10/1986 | Samson et al. . | |
| 4,669,465 | 6/1987 | Moore et al. . | |
| 4,721,117 | 1/1988 | Mar et al. | 600/585 |
| 4,723,936 | 2/1988 | Buchbinder et al. . | |
| 4,732,163 | 3/1988 | Bonello et al. | 128/772 |
| 4,748,986 | 6/1988 | Morrison et al. | 128/772 |
| 4,763,647 | 8/1988 | Gambale | 128/657 |
| 4,798,598 | 1/1989 | Bonello et al. . | |
| 4,830,023 | 5/1989 | de Toledo et al. . | |
| 4,832,047 | 5/1989 | Sepetka et al. | 128/772 |
| 4,846,186 | 7/1989 | Box et al. . | |
| 4,867,173 | 9/1989 | Leoni . | |
| 4,884,573 | 12/1989 | Wijay et al. . | |
| 4,884,579 | 12/1989 | Engelson . | |
| 4,922,924 | 5/1990 | Gambale et al. . | |
| 4,925,445 | 5/1990 | Sakamoto et al. . | |
| 4,940,062 | 7/1990 | Hampton et al. | 128/772 |
| 5,063,935 | 11/1991 | Gambale . | |
| 5,069,226 | 12/1991 | Yamauchi et al. . | |
| 5,107,852 | 4/1992 | Davidson et al. | 128/772 |
| 5,129,890 | 7/1992 | Bates et al. . | |
| 5,131,407 | 7/1992 | Ischinger et al. . | |
| 5,144,959 | 9/1992 | Gambale et al. . | |
| 5,174,302 | 12/1992 | Palmer | 128/772 |

(List continued on next page.)

FOREIGN PATENT DOCUMENTS

| | | |
|---|---|---|
| 0223179 | 11/1986 | European Pat. Off. . |
| 0142330 | 5/1997 | European Pat. Off. . |
| 2401668 | 8/1977 | France . |
| 9308862 | 5/1993 | WIPO . |

*Primary Examiner*—Max Hindenburg
*Assistant Examiner*—Pamela L. Wingood
*Attorney, Agent, or Firm*—Thomas R. Vigil; Dean Garner; Henry Collins

[57] ABSTRACT

The guidewire assembly includes a distal tip section comprising a core wire, a mushroom shaped head fixed to a distal end of the core wire, and a coiled radiopaque wire having a distal end portion fused to the head and a proximal necked down portion which necks down to proximal end coils forming a proximal end of the coiled radiopaque wire. The proximal end coils are received on a portion of the core wire and fixed thereto by a flexible material.

The method for making a guidewire assembly having increased flexibility and a secure connection between a coiled wire and a core wire comprises the steps of: forming a coiled radiopaque wire with a larger-in-diameter distal portion, a necked down middle portion, and a smaller-in-diameter proximal portion having a plurality of end coils; winding the end coils on a mandrel so that the end coils can form the proximal end portion of the coiled wire; pushing the end coils onto a tapered portion of a core wire; placing a flexible sleeve over the end coils; heat shrinking the flexible sleeve at one temperature; placing an outer sleeve over the flexible sleeve; and, heat shrinking the outer sleeve at a higher temperature to melt the flexible sleeve causing it to bond onto the tapered portion between the end coils and to the end coils.

9 Claims, 1 Drawing Sheet

U.S. PATENT DOCUMENTS

| | | |
|---|---|---|
| 5,176,149 | 1/1993 | Grenouillet . |
| 5,209,730 | 5/1993 | Sullivan . |
| 5,213,111 | 5/1993 | Cook et al. . |
| 5,228,453 | 7/1993 | Sepetka ................................. 128/772 |
| 5,241,970 | 9/1993 | Johlin, Jr. et al. . |
| 5,251,640 | 10/1993 | Osborne ................................ 128/772 |
| 5,253,653 | 10/1993 | Daigle et al. . |
| 5,259,393 | 11/1993 | Corso, Jr. et al. . |
| 5,267,574 | 12/1993 | Viera et al. ........................... 128/772 |
| 5,345,945 | 9/1994 | Hodgson et al. ..................... 128/772 |
| 5,353,808 | 10/1994 | Viera .................................... 128/722 |
| 5,368,049 | 11/1994 | Raman et al. . |
| 5,402,799 | 4/1995 | Colon et al. ......................... 128/657 |
| 5,406,960 | 4/1995 | Corso, Jr. . |
| 5,409,004 | 4/1995 | Sloan . |
| 5,409,015 | 4/1995 | Palermo ............................... 128/772 |

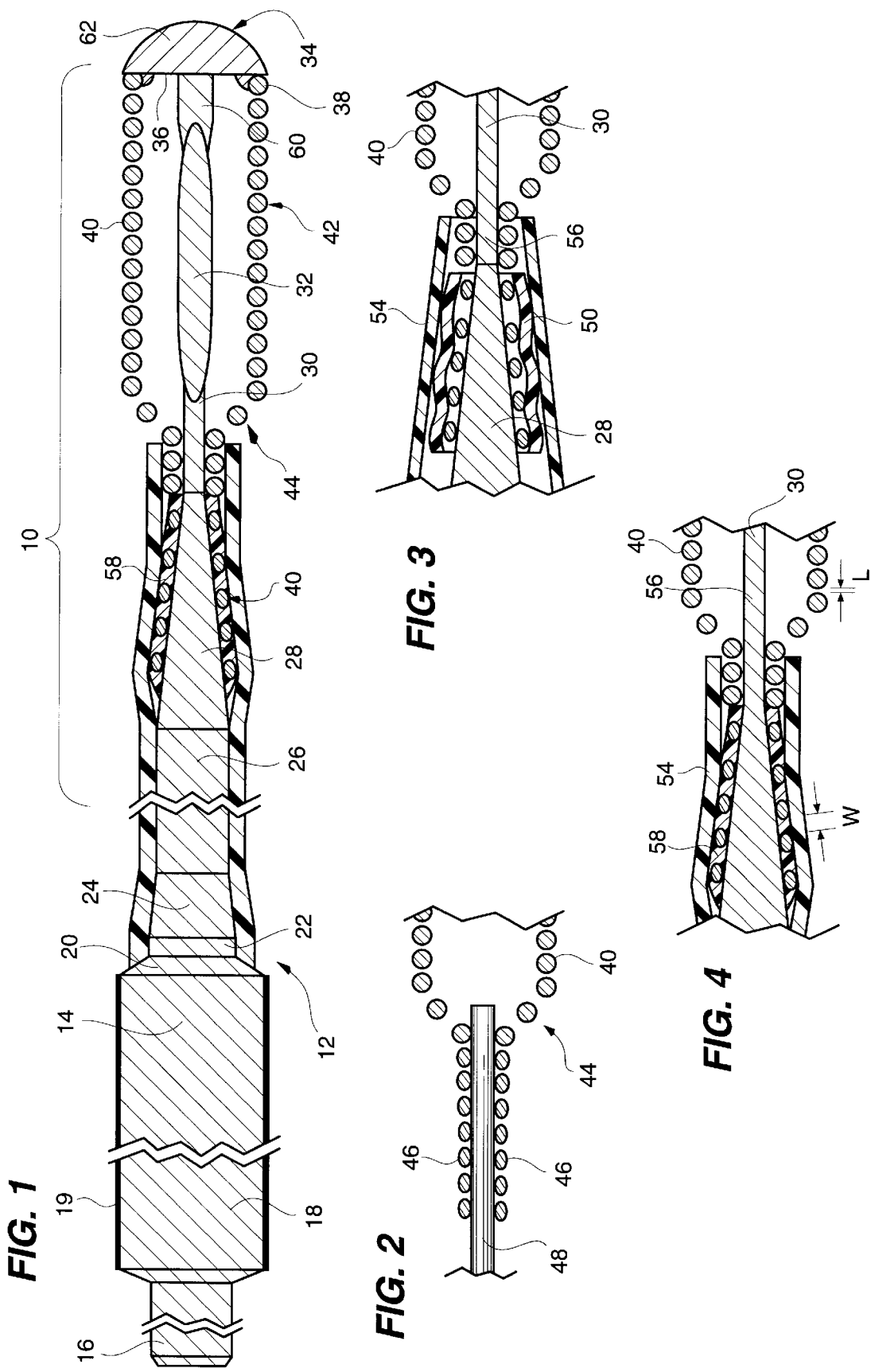

GUIDEWIRE ASSEMBLY

BACKGROUND OF THE INVENTION

1. Field of the Invention.

The present invention relates to a guidewire assembly for enhancing, in a tip section of the guidewire, the connection of a necked down proximal end portion of a coiled wire to a tapered portion of a core portion of a guidewire utilizing a nylon fusing sleeve for fusing the proximal end portion of the coiled wire to the tapered portion.

2. Description of the related art including information disclosed under 37 CFR §§ 1.97–1.99.

Heretofore various techniques have been proposed for securing a tapered portion of a core wire of a guidewire assembly to a coiled wire to ensure that if the core wire breaks, the broken segment does not separate from the remaining core wire and yet retains flexibility in a tip section of a guidewire.

Several techniques have been proposed for the construction of a tip section of a guidewire and examples of some of those techniques and constructions are disclosed in the following U.S. and foreign patents:

| U.S. Pat. No. | Patentee |
| --- | --- |
| Re.33,911 | Samson et al. |
| 4,538,622 | Samson et al. |
| 4,732,163 | Bonello et al. |
| 4,748,986 | Morrison et al. |
| 4,763,647 | Gambale et al. |
| 4,832,047 | Sepetka et al. |
| 4,940,062 | Hampton et al. |
| 5,174,302 | Palmer |
| 5,228,453 | Sepetka et al. |
| 5,267,574 | Viera et al. |
| 5,345,945 | Hodgson et al. |
| 5,353,808 | Viera |
| 5,402,799 | Colon et al. |
| 5,409,015 | Palermo et al. |
| Foreign Publications: | |
| EP 0 142 330 | Samson et al. |

The Gambale et al. U.S. Pat. No. 4,922,924 discloses a distal brazed joint between a coil and a core wire or shaft and a proximal adhesive joint between the coil and a larger-in-diameter portion of the shaft.

The Viera et al. U.S. Pat. No. 5,267,574 discloses a necked down portion of a coiled wire and proximal end coils of the necked down coiled wire held to a distal end of a core wire by a polytetrafluorethylene sleeve heat shrunk around the proximal end coils.

The Viera U.S. Pat. No. 5,353,808 shows a solder connection between coils of a coiled wire and a tapered portion of a core wire in a guidewire assembly.

The Morrison et al. U.S. Pat. No. 4,748,986 shows a brazed connection between a coil and a tapered portion of a flexible elongate element (core wire) of a guidewire assembly.

The Sepetka et al. U.S. Pat. No. 4,832,047 teaches fixing of flattened coils at the proximal end of a coil to a tapered distal end portion of a core wire by a soldered or welded connection to the core wire.

The Palermo et al. U.S. Pat. No. 5,409,015 teaches a soldered joint between an outer fine wire coil and a distal tapered portion of a metal guidewire core.

As will be described in greater detail hereinafter, the guidewire assembly of the present invention provides a flexible attachment and method for attaching a necked down proximal end portion of a radiopaque platinum tungsten coiled wire to a tapered portion of a stainless steel core wire using a heat shrinkable and meltable plastic sleeve.

SUMMARY OF THE INVENTION

According to the teachings of the present invention there is provided a guidewire assembly including a distal tip section including a core wire, a mushroom shaped head fixed to a distal end of the core wire, and a coiled radiopaque wire having a distal end portion fused to the head and a proximal necked down portion which necks down to proximal end coils forming a proximal end of the coiled radiopaque wire. The proximal end coils are received on a portion of the core wire and fixed thereto by a flexible material which extends into the space between the proximal end coils.

Further according to the present invention there is provided a method for making an enhanced guidewire assembly having increased flexibility and a secure connection between a coiled wire and a core wire comprising the steps of: forming a coiled radiopaque wire with a larger-in-diameter distal portion, a necked down middle portion, and a smaller-in-diameter proximal portion having a plurality of proximal end coils; winding the end coils on a mandrel so that the end coils can form the proximal end portion of the coiled wire; pushing the proximal end coils onto a tapered portion of a core wire; placing a flexible sleeve over the flattened end coils; heat shrinking the flexible sleeve at one temperature; placing an outer sleeve over the flexible sleeve; and, heat shrinking the outer sleeve at a higher temperature to melt the flexible sleeve causing it to bond onto the tapered portion between the end coils and to the end coils.

BRIEF DESCRIPTION OF THE DRAWINGS

FIG. 1 is a longitudinal sectional view through the tip section of the guidewire assembly constructed according to the teachings of the present invention.

FIG. 2 is a fragmentary sectional view of the proximal end of the necked down coiled wire shown in FIG. 1 after the proximal end coils have been flattened and then wound on a mandrel.

FIG. 3 is a fragmentary, sectional view of a second tapered portion of the core wire, shows the flattened coils pushed onto the second tapered portion of the core wire of the guidewire, shows a nylon sleeve heat shrunk over the flattened coils and shows a polytetrafluorethylene (Teflon™) sleeve placed thereover prior to heat shrinking.

FIG. 4 is a fragmentary, sectional view of the second tapered portion of the core wire, shows the flattened end coils on the second tapered portion of the core wire of the guidewire and shows the polytetrafluorethylene (PTFE) sleeve heat shrunk over the nylon sleeve heat causing it to melt and form a glue or adhesive between the PTFE sleeve, the flattened end coils and the second tapered portion of the core wire of the guidewire assembly.

DESCRIPTION OF THE PREFERRED EMBODIMENT(S)

Referring now to the drawings in greater detail, there is illustrated in FIG. 1 a longitudinal sectional view of a tip section 10 of a guidewire assembly 12 constructed according to the teachings of the present invention. The guidewire assembly 12 includes a stainless steel core wire 14 comprising a proximal first uniform diameter portion 16, a middle larger-in-diameter portion 18 coated with a layer 19 of polytetrafluorethylene, a necked down portion 20, a first reduced-in-diameter portion 22, a first tapered portion 24, a second reduced-in-diameter portion 26 having a diameter similar to the first proximal portion 16, a second tapered portion 28, and a rod tip portion 30 which can have a nub or cylinder 32 and which extends to a mushroom shaped tip 34. Fixed or fused to a back side 36 of the mushroom shaped tip 34 is a distal coil 38 of a coiled platinum or platinum tungsten (92% platinum and 8% tungsten) wire 40 that has a diameter of approximately 0.003 inch and that includes a coiled distal portion 42 with a uniform diameter extending proximally to a necked down portion 44 that extends downwardly to a proximal portion 46 including reduced-in-diameter proximal end coils 46.

According to the teachings of the present invention the proximal end coils 46 are flattened, stretched out and then wound on a mandrel 48, shown in FIG. 2. Then the proximal end coils 46 are pushed over the second tapered portion 28, as shown in FIG. 3 to establish an interference fit between the end coils 46 and the second tapered portion 28, thereby to firmly hold the end coils 46 to the core wire 14. On the second tapered end portion 28, the turns or end coils 46 are spaced apart a distance W of between approximately 0.010 to 0.015 inch and preferably only 0.010 inch.

Then, according to the teachings of the present invention and as shown in FIG. 3, a nylon sleeve 50 is heat shrunk over the end coils 46 on the second tapered portion 28, at a temperature of approximately 350° F, thereby to extend between the end coils 46 and to the second tapered portion 28 of the core wire 14. Next, a sleeve 54 of polytetrafluorethylene-PTFE (Teflon™) is placed over a proximal end 56 of the rod tip portion 30, the second tapered portion 28, the second reduced-in-diameter portion 26, the first tapered portion 24 and the first reduced-in-diameter portion 22 and heat shrunk, as shown in FIG. 1 and in FIG. 4 at a temperature of approximately 700° F, above the melting point of 400° F for nylon, and, in the process, melting the nylon sleeve 50 to a glue 58 causing it to flow between the stretched out, spaced apart, flattened end coils 46 like a glue or adhesive 58 and adhere to the flattened end coils 46 and to the second tapered portion 28, thereby to fix the end coils 46 to the core wire 14.

While the nylon sleeve 50 is preferred, sleeves of other materials, such as polyurethane and polyvinylchloride (PVC) could be utilized. The material is preferably a heat shrinkable thermoplastic material.

The mushroom shaped tip 34 is formed by a fusing or melting of distal coils of the coiled platinum wire 40 to the nub or cylinder 32 at the outer end of the stainless steel rod tip portion 30 so as to form the mushroom tip 34 with a stem 60 slightly larger in diameter than the proximal end 56 of the rod tip portion 30 and a mushroom shaped head 62 made of fused platinum and stainless steel. The distal coils are spaced apart a distance L of approximately 0.001 inch.

The fixing of the flattened end coils 46 with the melted nylon, which serves as a hot glue 58, to the second tapered portion 28 has the advantage of maintaining flexibility and pliability in the connection of the flattened end coils 46 to the second tapered portion 28 and avoid the stiffness obtained when such end coils are brazed, welded or soldered to a core wire.

From the foregoing description, it will be appreciated that the guidewire assembly 12, and particularly the tip section 10 thereof, has a number of advantages, some of which have been described above and other of which are inherent in the invention. Accordingly, the scope of the invention is only to be limited as necessitated by the accompanying claims.

We claim:

1. A guidewire assembly including a distal tip section including a core wire having a distal end, a head connected to said distal end of said core wire, said core wire extending form said distal end to a first proximal portion which extends to a second proximal main body portion, and a coiled radiopaque wire having a distal end portion fixed to said head and a proximal necked down portion which necks down to proximal end coils forming a proximal end of the coiled radiopaque wire, said proximal end coils being received on said first proximal portion of said core wire; a short sleeve of thermoplastic material received over said proximal end coils received on said first proximal portion and melted over and between said proximal end coil for fixing same onto said first proximal end of said core wire; a sleeve of heat shrinkable material received over said proximal end coils and said first proximal portion and said proximal main body portion and heat shrunk over at least said first proximal portion to cause melting of said short sleeve of thermoplastic material into the spaces between coils of said proximal end coils.

2. The guidewire assembly of claim 1 wherein said proximal end coils are flattened.

3. The guidewire assembly of claim 1 wherein said first proximal portion of said core wire is a tapered portion which is tapered from said second proximal main body portion which has a larger diameter to a distal smaller diameter portion.

4. The guidewire assembly of claim 1 wherein said short sleeve is made of nylon.

5. The guidewire assembly of claim 1 wherein said melted material of said short sleeve extends into the space between proximal end coils and to said first proximal portion of said core wire and is adhered thereto.

6. The guidewire assembly of claim 1 wherein said end coils are spaced apart approximately 0.01 to 0.015 inch.

7. The guidewire assembly of claim 1 wherein said end coils are spaced apart no more than 0.01 inch.

8. The guidewire assembly of claim 1 wherein coils in said distal end portion of said coiled radiopaque wire are spaced apart approximately 0.001 inch.

9. The guidewire assembly of claim 1 wherein said coiled radiopaque wire has a diameter of approximately 0.003 inch.

* * * * *